United States Patent [19]

Kambara et al.

[11] Patent Number: 4,675,095
[45] Date of Patent: Jun. 23, 1987

[54] FLUORESCENCE DETECTION TYPE ELECTROPHORETIC APPARATUS

[75] Inventors: Hideki Kambara, Hachioji; Jirou Tokita, Kokubunji; Tamotu Simada, Akishima; Ken'ichi Watanabe, Kokubunji, all of Japan

[73] Assignee: Hitachi, Ltd., Tokyo, Japan

[21] Appl. No.: 763,610

[22] Filed: Aug. 8, 1985

[30] Foreign Application Priority Data

Aug. 13, 1984 [JP] Japan .............................. 59-167812

[51] Int. Cl.$^4$ ...................... B01D 57/02; G01N 27/26
[52] U.S. Cl. .............................. 204/299 R; 204/182.8
[58] Field of Search ............ 204/299 R, 182.8, 183.3, 204/182.9, 183.2, 180.1

[56] References Cited

U.S. PATENT DOCUMENTS

| | | | |
|---|---|---|---|
| 3,793,180 | 2/1974 | Flower et al. | 204/299 R |
| 3,870,612 | 3/1975 | Flygare et al. | 204/299 R X |
| 4,011,044 | 3/1977 | Uzgiris | 204/299 R X |
| 4,046,667 | 9/1977 | Goetz | 204/299 R |
| 4,113,596 | 9/1978 | Treille et al. | 204/299 R X |

OTHER PUBLICATIONS

Maxam-Gilbert, DNA (Protein.Nucleic Acid.Enzyme) vol. 23, No. 3 (1978) pp. 182-196.

*Primary Examiner*—John F. Niebling
*Assistant Examiner*—John S. Starsiak, Jr.
*Attorney, Agent, or Firm*—Antonelli, Terry & Wands

[57] ABSTRACT

An electrophoretic apparatus according to this invention comprises electrophoretic paths along which sample fragments labeled with phosphor migrate; electrodes disposed at both the ends of said electrophoretic paths; a driving power source for giving said sample fragments on the electrophoretic paths electrophoretic force by applying an electric potential difference between said electrodes; an excitation light source projecting an excitation light to said sample fragments on said electrophoretic paths; and means for detecting fluorescence emitted by the phosphor existing in the sample fragments and excited by the excitation light. Said an excitation light source is so disposed that the excitation light is projected to said sample fragments on said electrophoretic paths in a direction substantially parallel to a plane containing said electrophoretic paths.

5 Claims, 6 Drawing Figures

FIG. IA (PRIOR ART)
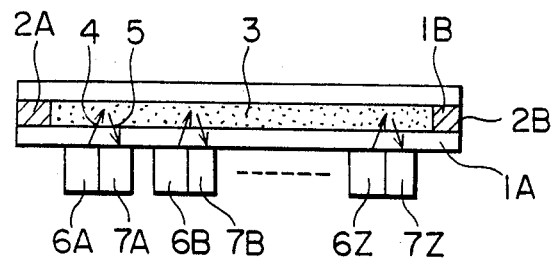
FIG. IB (PRIOR ART)
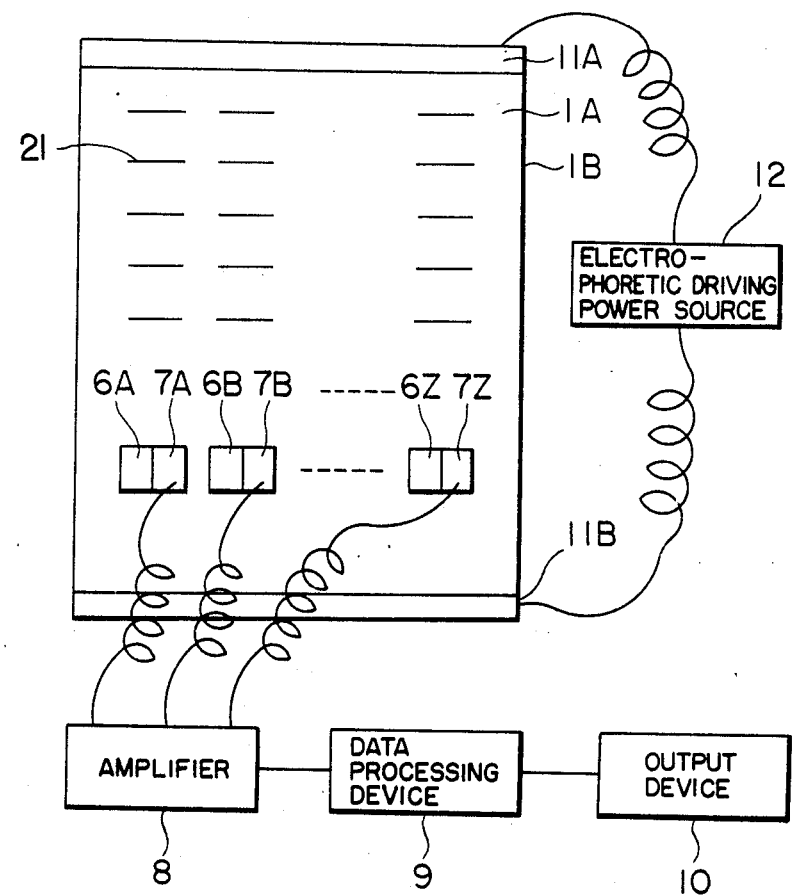

FLUORESCENCE DETECTION TYPE ELECTROPHORETIC APPARATUS

BACKGROUND OF THE INVENTION

This invention relates to an apparatus for separating and detecting substances relative to a living body such as DNA (deoxyribonucleic acid), RNA (ribonucleic acid), etc. and in particular to a fluorescence detection type electrophoretic apparatus for analyzing the structure such as a base sequence in these substances by detecting fluorescence.

Heretofore the method, by which a substance to be examined is labeled with radioactive phosphorus ($^{32}P$), is utilized widely for determining the sequence of bases constituting a substance such as DNA (Tampakushitsu.-Kakusan. Kohso (Protein.Nucleic Acid.Enzyme) Vol. 23, No. 3, p. 182 (1978)). By this method utilizing a radioactive label, one end of the substance such as DNA, etc., whose structure is to be determined, is labeled with $^{32}P$ and after that, the substance is cut by provoking particular chemical reactions at certain positions of the bases by using a restriction enzyme. By controlling the rate of this chemical reaction, it is possible to produce fragments having $^{32}P$ at the end, which have various lengths and each of which has a specified base at its severed end. They are separated by electrophoresis and detected by means of photographic plates, etc. This method has a disadvantage that a radioactive substance must be used and therefore a method, by which a substance to be examined is labeled with phosphor instead of radioactive substance and detected optically, is studied. In the case where phosphor is used for labeling, important problems for increasing detection sensitivity to fluorescence are how background noise can be reduced and how DNA etc., to which phosphor is added, are excited with a high efficiency.

In order to excite DNA fragments, to which phosphor is added, with light and to detect fluorescence thus emitted, the method as illustrated in FIGS. 1A and 1B is used. That is, light emitted from an excitation light source 6A passes a glass plate 1A and is projected into the gel portion 3. Further it passes another glass plate 1B and goes out into the exterior. If there exists a DNA fragment 21 in the path of the excitation light in the gel portion 3, the fragment is excited by the light and emits fluorescence, which is detected by a detector 7A. The output of the fluorescence detector 7A is treated by a data processing device 9, after having been amplified by an amplifier 8, and finally is displayed or printed out by an output device 10.

However, for this method, it is necessary to provide each of a plurality of electrophoretic paths with a light source or to divide a light beam emanating from one light source by means of mirrors, etc. to irradiate each fragment. Accordingly it has a disadvantage that the quantity of excitation light per fragment is reduced or the apparatus has a complicated structure. Further it has another disadvantage that, apart from fluorescence emitted by DNA fragments, to which phosphor is added, reflected light and fluorescence due to the glass plates holding electrophoretic gel give rise to background noise, which prevents measurements with a high sensitivity.

SUMMARY OF THE INVENTION

This invention has been done in order to remove these disadvantages and its object is to provide a fluorescence detection type electrophoretic apparatus permitting to excite a plurality of DNA bands by means of a light source, producing only low background noise, without using a plurality of excitation light sources.

Background noise consists principally of fluorescence and scattered light produced by glass plates at both the sides holding the gel, and of fluorescence and scattered light emitted by the gel itself. Consequently, in order to eliminate the background noise due to the glass plates, this invention is characterized in that incident excitation light is projected through a gap between the two glass plates substantially parallel to the boundary planes of the gel and that fluorescence is detected in the direction perpendicular to the path of the excitation light. In this way, fluorescence produced in the glass plates is reduced and at the same time augmentation of the background noise due to scattering is prevented.

BRIEF DESCRIPTION OF THE DRAWINGS

FIGS. 1A and 1B are a transversal cross-sectional view and a front view, respectively, of a prior art apparatus, in which each of electrophoretic paths is provided with an excitation light source and a light detector;

DESCRIPTION OF THE PREFERRED EMBODIMENT

Figure 2:
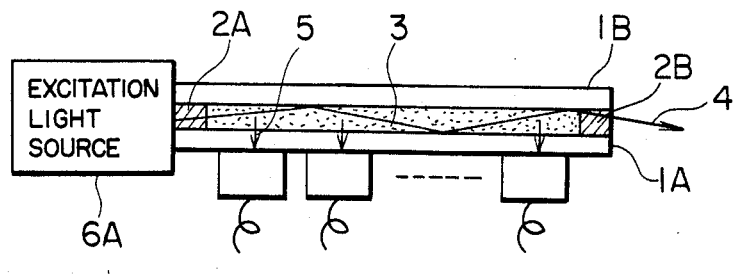
FIG. 2 is a transversal cross-sectional view of an electrophoretic apparatus according to an embodiment of this invention.
Figure 3:
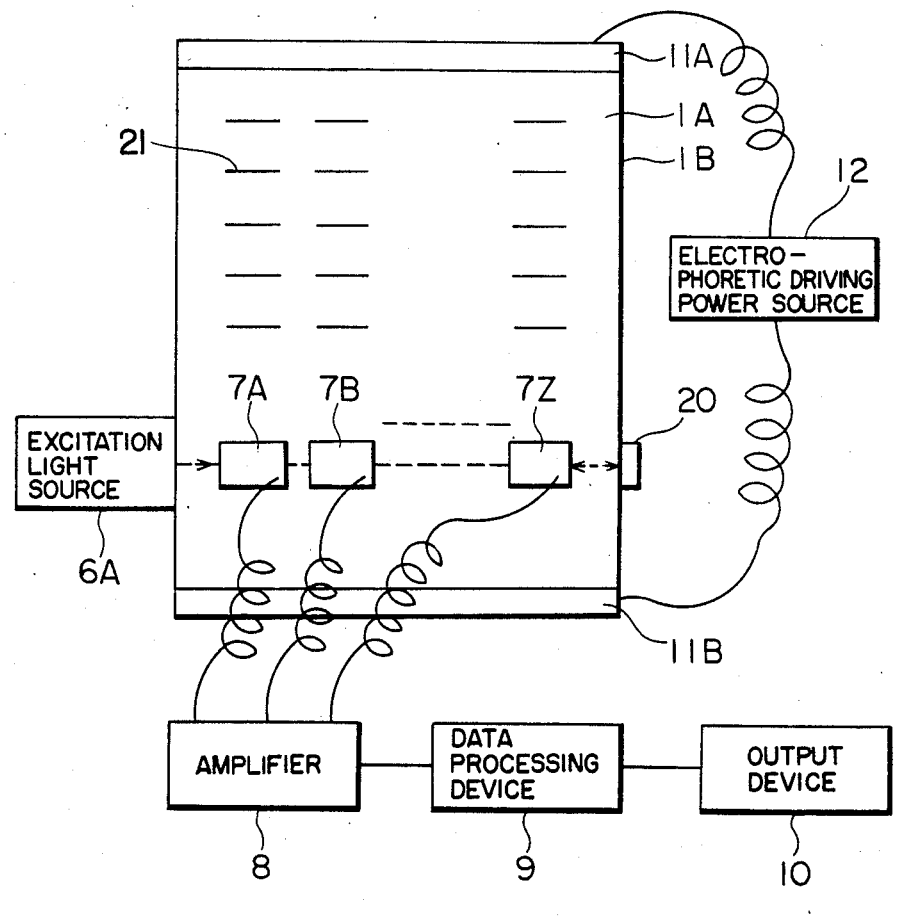
FIG. 3 is a front view of the electrophoretic apparatus illustrated in FIG. 2.

FIGS. 2 and 3 show schematically an electrophoretic apparatus according to this invention and they are a transversal cross-sectional and a front view, respectively.

Two plain plates 1A and 1B are held parallel to each other with a certain distance by means of two spacers 2A and 2B. In this case, the plain plate 1A, the spacers 2A and 2B are transparent with respect to the excitation light, and the plain plate 1B can be either transparent or opaque. The space enclosed by the plain plates 1A, 1B and the spacers 2A, 2B is filled with polyacrylamide or agarose gel 3. At the upper and the lower end of the plain plates 1A and 1B are mounted two electrodes 11A and 11B each through a buffer solution cell, between which an electrophoretic driving power source 12 is connected for giving the sample to be examined the electrophoretic force. In FIG. 3, the sample migrates in the vertical direction.

Figure 4:
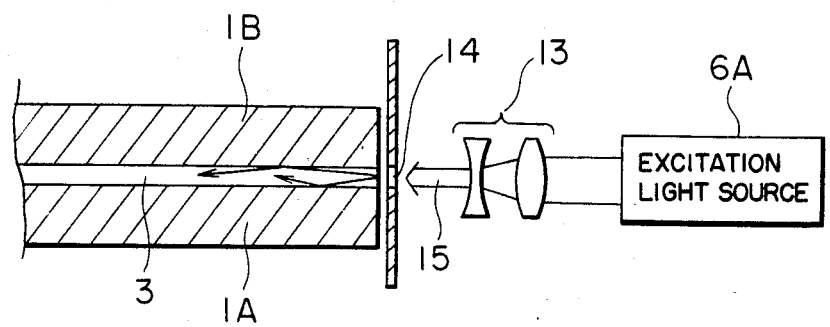
FIGS. 4 and 5 are cross-sectional views of an excitation optical system and a detection optical system, respectively, according to an embodiment of this invention.

When a sample is poured in the electrophoretic cell, according to the size of molecules of the sample, the smaller the molecule is the faster it migrates. The migration takes place along electrophoretic paths which are substantially perpendicular to equi-potential lines. That is, for a sample containing molecules having various sizes, the smaller the molecule is, the earlier it migrates along the electrophoretic paths, in the order of the molecular weight. The molecules of the sample are detected one after another in ascendent order of the molecular weight by labeling them with phosphor and providing the electrophoretic paths with an excitation light irradiation and fluorescence detection function. In order to enable this, an excitation light source 6A is disposed at an appropriate location on one side of the plain plate 1A, 1B. As the excitation light source 6A, lasers or various sorts of lamps can be used. In any case, the excitation light must be collimated so as to be a narrow beam and at the same time shaped so as to be a parallel beam by means of a lens, etc. An embodiment of the optical system for projecting the excitation light to the electrophoretic gel according to this invention will be explained, referring to FIG. 4. In the figure, the optical system for the excitation consists of an excitation light source, e.g. a laser oscillator 6A, a focusing lens 13 and a slit 14. The focusing lens 13 can be e.g. a cylindrical lens and the slit 14 can be formed in a shielding metal plate. In this way, the beam 15 emitted from the excitation light source 6A can be projected to the gel portions 3 with a width equal to or smaller than that thereof.

In addition, in the case where the diameter of the light beam is greater than the distance between the two plain plates 1A and 1B, the light beam is shaped by means of a slit, etc. so that light is projected only to the gel portion. The light beam having a divergence angle larger than a predetermined value is shielded by the shielding metal plate, etc. so that the angle of the incident beam is larger than the critical angle of total internal reflection determined by the refractive index of the gel and that of the plain plates 1A, 1B with respect to the incident light. That is, the two plain plates 1A, 1B constitute a sort of optical guide, within which an electrophoretic part is formed.

In the case where the sequence of bases such as DNA, etc. is determined, a plurality of samples are made to migrate simultaneously along electrophoretic paths, as illustrated in FIG. 3. In this case, it is possible to excite a plurality of DNA bands simultaneosuly by making light enter at one side of the gel part in the direction perpendicular to the migration direction. At the intersection of the excitation light beam and each of the migration electrophoretic paths is disposed each of the fluorescence detectors 7A–7Z.

The excitation light is projected at one side and passes through the gel. In this case, the light components diverging towards the outside of the boundary planes of the gel reach the other side of the gel while being totally reflected by the plates holding the gel such as glass plates. At the other side is disposed a reflecting mirror 20 or another light source so that the excitation efficiency is increased.

The outputs of the fluorescence detectors are treated in a data processing device 9 after having been amplified in an amplifier 8 and displayed or printed out by an output device 10.

Figure 5:
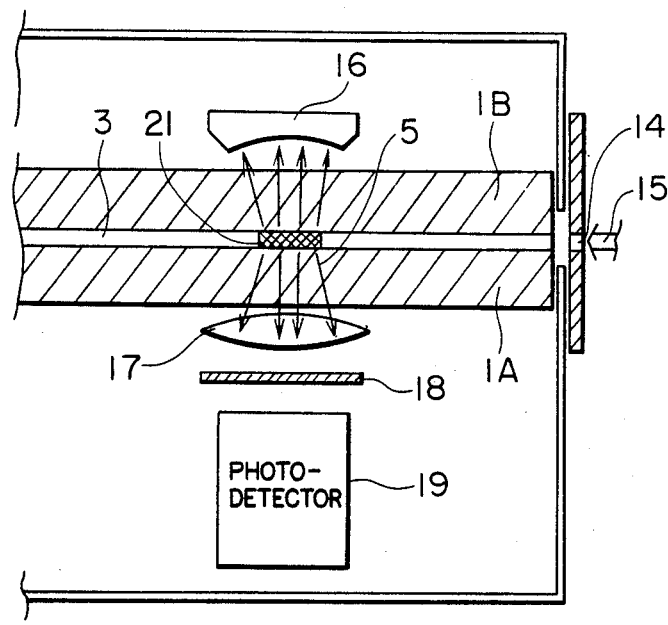

An embodiment of the fluorescence detector will be explained below, referring to FIG. 5. Since fluorescence 5 emitted by a DNA band fragment 21 according to this invention is weak, a focusing lens 17 having a large aperture is necessary to collect fluorescence light as much as possible. For increasing the sensitivity it is also important to collect fluorescence emitted through the glass plate 1B by means of a minor mirror 16. Light components having wavelengths different from that of the fluorescence are removed by a filter 18. As a photodetector 19 an opto-electric conversion element can be used. Especially it is desirable to use a photomultiplier tube having high sensitivity characteristics.

According to this invention, the following advantages can be obtained:

(i) Background noise entering the detector can be reduced and the fluorescence detection method can be applied, using no radioisotope, because only the necessary part is irradiated efficaciously with excitation light; and (ii) Many DNA fragment bands can be excited simultaneously for determining the sequence of DNA bases and thus it is possible to analyze simultaneously the sequence of various DNAs.

We claim:

1. A fluorescence detection electrophoretic apparatus comprising:
    means for providing a plurality of substantially parallel electrophoretic paths along which sample fragments labeled with phosphor migrate, said electrophoretic paths being substantially disposed in a plane,
    electrodes disposed at both opposite ends of said electrophoretic paths;
    a driving power source for giving said sample fragments on said electrophoretic paths electrophoretic force by applying an electric potential across said electrodes;
    excitation light source means for projecting a common excitation light to said electrophoretic paths in a direction substantially perpendicular to a direction of migration of said sample fragments; and
    means for detecting fluorescences emitted from the phosphors existing in the sample fragments by the excitation light with respect to the respective electrophoretic paths, independently of each other.

2. A fluorescence detection electrophoretic apparatus according to claim 1, wherein each of said means for detecting fluorescence is disposed in front of each of said electrophoretic paths.

3. A fluorescence detection electrophoretic apparatus according to claim 1, further comprising means respectively provided adjacent to each of said electrophoretic paths for collecting and directing to said fluorescence detecting means the fluorescences emitted from the sample fragments migrating along an associated path.

4. A fluorescence detection electrophoretic apparatus according to claim 1, wherein said excitation light source means is arranged to project the common excitation light onto the sample fragments on all of said electrophoretic paths simultaneously at positions spaced from respective starting ends of said electrophoretic paths, by equal distances.

5. A fluorescence detection electrophoretic apparatus according to claim 1, wherein said excitation light source means projects said common excitation light to said electrophoretic paths in a direction substantially parallel to the plane containing said electrophoretic paths.

* * * * *